(12) United States Patent
Dyckman et al.

(10) Patent No.: US 7,102,036 B2
(45) Date of Patent: Sep. 5, 2006

(54) PROCESS AND CATALYST FOR PURIFYING PHENOL

(75) Inventors: Arkady Samuilovich Dyckman, Saint Petersburg (RU); John William Fulmer, Mt. Vernon, IN (US); Boris V. Krasy, Saint Petersburg (RU); Viktor Vladimirovich Pinson, Saint Petersburg (RU); Yury Alekseevich Shavandin, Saint Petersburg (RU); Genrikh Petrovich Yavshits, Saint Petersburg (RU); Andrey Vladimirovich Zinenkov, Saint Petersburg (RU)

(73) Assignee: General Electric Company, Schenectady, NY (US)

( * ) Notice: Subject to any disclaimer, the term of this patent is extended or adjusted under 35 U.S.C. 154(b) by 674 days.

(21) Appl. No.: 10/354,270

(22) Filed: Jan. 30, 2003

(65) Prior Publication Data

US 2003/0163007 A1    Aug. 28, 2003

(30) Foreign Application Priority Data

Feb. 8, 2002    (RU) ............................... 2002103669

(51) Int. Cl.
*C07C 37/08* (2006.01)
*C07C 37/68* (2006.01)
(52) U.S. Cl. .................. 568/754; 568/716; 568/749
(58) Field of Classification Search ............... 568/749, 568/750, 754, 716
See application file for complete search history.

(56) References Cited

U.S. PATENT DOCUMENTS

| | | | |
|---|---|---|---|
| 2,441,408 A | 5/1948 | Goldblum |
| 2,734,085 A | 2/1956 | Adams et al. |
| 2,744,143 A | 5/1956 | Filar |
| 2,910,511 A | 10/1959 | Joris |
| 2,992,169 A | 7/1961 | Gregory et al. |
| 3,335,070 A | 8/1967 | Adams |
| 3,437,699 A | 4/1969 | Flickinger |
| 3,466,260 A | 9/1969 | Bostian et al. |
| 3,545,653 A | 12/1970 | Larson |
| 3,692,845 A | 9/1972 | Cheema et al. |
| 3,862,244 A | 1/1975 | Genod et al. |
| 3,931,339 A | 1/1976 | Cooke |
| 3,965,187 A | 6/1976 | Little et al. |
| 4,092,360 A | 5/1978 | Van Peppen et al. |
| 4,251,325 A | 2/1981 | Marsh et al. |
| 4,298,765 A | 11/1981 | Cochran et al. |
| 4,334,107 A | 6/1982 | Van Peppen |
| 4,409,412 A | 10/1983 | Haag et al. |
| 4,906,791 A | 3/1990 | Imanari et al. |
| 4,973,766 A | 11/1990 | Penzo et al. |
| 5,091,058 A | 2/1992 | Davie |
| 5,185,475 A | 2/1993 | Kissinger |
| 5,262,016 A | 11/1993 | Lorenzoni et al. |
| 5,264,636 A | 11/1993 | Shirahata et al. |
| 5,304,689 A | 4/1994 | Kissinger |
| 5,414,154 A | 5/1995 | Jenczewski et al. |
| 5,491,268 A | 2/1996 | Cipullo |
| 5,502,259 A | 3/1996 | Zakoshansky et al. |
| 5,510,543 A | 4/1996 | Fulmer et al. |
| 6,066,767 A | 5/2000 | Zakoshansky et al. |
| 6,201,157 B1 | 3/2001 | Keenan |
| 6,326,328 B1 | 12/2001 | Matsuzawa |
| 6,448,453 B1 | 9/2002 | Oberholtzer et al. |

FOREIGN PATENT DOCUMENTS

| | | |
|---|---|---|
| FR | 1 445 829 A | 7/1966 |
| GB | 1108327 | 4/1968 |
| RU | 2058189 C1 | 4/1996 |
| RU | 1559494 A1 | 2/1997 |

OTHER PUBLICATIONS

J.C. Yori, M.A. D'Amato, G. Costa and J. M. Parera, Journal of Catalysis 153, 218-223 (1995).
U.S. Appl. No. 09/683190, filed Nov. 29, 2001, System and Method for Purifying Cumene Hydroperoxide Cleavage Products, Fulmer et al.
Patent Abstracts of Japan, Publication No. JP60132650, publication date, Jul. 15, 1985.

*Primary Examiner*—Elvis O. Price

(57) ABSTRACT

The goal of this invention is to produce phenol of high purity by conversion of impurities that are present in the starting phenol, which is produced by the decomposition of cumyl hydroperoxide. The indicated goal is achieved by purifying the phenol containing admixtures of aliphatic and aromatic carbonyl compounds with an aluminum zirconium catalyst.

3 Claims, No Drawings

PROCESS AND CATALYST FOR PURIFYING PHENOL

The present application is a U.S. non-provisional application based upon and claiming priority from Russian Application No.2002103669, with a filing date of Feb. 8, 2002, which is hereby incorporated by reference.

BACKGROUND

The invention relates to the area of chemistry and petrochemistry, more precisely to a process for producing phenol and acetone by the cumene method.

The phenol that is used as the starting material, which is produced by the decomposition of cumyl hydroperoxide with an acidic catalyst, does not satisfy consumer requirements, since it contains admixtures of hydroxyacetone (HA), 2-methylbenzofuran (2-MBF), α-methylstyrene (AMS), acetophenone (AP), mesityl oxide (MO), and dimethylphenylcarbinol (DMPC), and needs to have the indicated impurities removed.

Relatively pure end product phenol is obtained by means of fractional distillation of the decomposition product of cumyl hydroperoxide with separation from the lower-boiling and higher-boiling components [U.S. Pat No. 4,251,325 (1978)]. However, even with careful operation of the rectifier, the phenol that is isolated contains such impurities as HA and 2-methylbenzofuran in quantities which are relatively small, but are still undesirable.

Processes are known for purifying the phenol that is used as the starting material which involve the use of various heterogeneous catalysts which convert the impurities listed above almost entirely into high-boiling compounds which can later be separated from the product phenol by distillation. One exception is HA, which can be converted into 2-methylbenzofuran or into higher-boiling products, depending on the efficiency of the catalyst. Thus, during the catalytic conversion the only impurity—2-methylbenzofuran—can accumulate in the catalysis product, complicating the subsequent separation process.

For example, a process is known for producing phenol of high purity from the phenol that is used as the starting material, which is produced by the decomposition of cumyl hydroperoxide with an acidic catalyst, by placing it in contact with a heterogeneous catalyst, which is a gamma aluminum oxide having a certain specific surface and a certain acidity of the surface centers. In the process, the aliphatic and aromatic carbonyl compounds, which are present in the starting phenol, are converted into high-boiling products, which are relatively easily removed from the end product by rectification [U.S. Pat. No. 5,264,636 (1992)]. The disadvantage of this process is the insufficiently high activity of the catalyst, especially when the content of impurities in the starting phenol is relatively small (0.1% by mass and less), which means that the 2-methylbenzofuran content of the end product is reduced to only a small extent.

A process is also known where phenol is purified by removing from it the side products of the cumene oxidizing process. This process involves treating the starting phenol by placing it in contact with a catalyst which is activated aluminosilicate, and then separating the resulting high-boiling components by distillation [U.S. Pat. No. 2,910,511 (1956)—prototype].

SUMMARY

The goal of this invention is to produce phenol of high purity by conversion of impurities that are present in the starting phenol, which is produced by the decomposition of cumyl hydroperoxide. The indicated goal is achieved by purifying the phenol containing admixtures of aliphatic and aromatic carbonyl compounds with an aluminum zirconium catalyst.

DETAILED DESCRIPTION

The catalyst which the prototype uses is a synthetic acidic aluminosilicate catalyst, which is amorphous or crystalline and which is produced either from a gel or by means of acid treatment of aluminosilicate clays of the bentonite type.

An effective temperature for the purification process is 50–200° C., which makes it possible to carry out the purification both in the liquid and the gaseous phase. The higher the activity of the catalyst and the higher the process temperature, the less contact time is required to achieve the necessary degree of purification of the phenol. However, as the catalyst is used, it is gradually deactivated as a consequence of its deposit in the pores of reaction products, which are in the solid state at the process temperature. Regenerating the catalyst involves washing it with purified phenol.

The disadvantage of this process for purifying phenol is also that the HA which is present is converted to a significant extent (up to 80%) by the aluminosilicate catalyst into 2-methylbenzofuran, which is difficult to remove from phenol.

The aluminum zirconium catalyst represents a mixture of zirconium oxides and sulfates, with the total content of aluminum and zirconium sulfates being from 5 to 15% by mass (calculated on the basis of $SO_4$) and the total content of aluminum oxide and sulfate being 5–30% by mass (calculated on the basis of aluminum oxide).

The process is carried out at a temperature of 90–200° C. and a relative raw material volumetric feed rate was maintained through the catalyst bed as necessary to provide a space velocity of 1 to 6 $h^{-1}$. The phenol which is produced by coming in contact with the proposed catalyst can be distilled to isolate practically pure phenol.

The impurities contained in the starting phenol are completely converted into high-boiling compounds which are easily separated from the phenol; this is also true of HA, not more than 30% of which is converted into 2-methylbenzofuran.

The essential characterizing features of the proposed process for purifying phenol are the use of an aluminum zirconium catalyst, which is a mixture of aluminum and zirconium oxides and sulfates, and carrying out the process at a given temperature and a given relative raw material volume feed rate.

This invention relates to a catalyst for purifying phenol and to a process for preparing it.

Aluminum oxide catalysts are usually prepared by precipitating aluminum hydroxide from a solution of sodium aluminate, using concentrated nitric acid at a pH of 8.7–9.5, using two methods: so-called "cold" precipitation at 18–25° C. and so-called "hot" precipitation at 100–102° C., and mixing these precipitates in different proportions, which makes it possible to control the quality of the product. The precipitate mixture is washed with water to remove sodium nitrate, plasticized by boiling it and peptizing it, and then the resulting mass is molded in screw extruders into granules of the required size [USSR patent no. 1559494 (1990), Russian Federation patent no. 2058189, published in *Biulleteń izobretenii* [Russian Patent Office Journal] no. 11 on Apr. 20, 1996].

Aluminum zirconium catalysts, which are used for other purposes, but not for the purification of phenol, are prepared by the process of precipitating zirconium hydroxide from a solution of zirconium oxychloride ($ZrOCl_2.8H_2O$) with an aqueous ammonia solution and then drying the resulting precipitate and treating it with 1 N sulfuric acid. For molding into granules, the sulfonated powdered zirconium hydroxide is mixed with aluminum hydroxide, which is used as a binder [*J. Catal.* 153:218–223 (1995)].

For example, a process is known of preparing an aluminum zirconium catalyst for isomerization of paraffin hydrocarbons [U.S. Pat. No. 6,326,328 (2000)—prototype]. The indicated process involves taking a mixture of powdered zirconium and aluminum hydroxides with the addition of a sulfating agent—ammonium sulfate salts, mixing it, extruding it, and roasting the resulting granules at 600° C. Aluminum hydroxide or hydrated aluminum hydroxide is used as a binder. However, the catalyst prepared according to this process is not suitable for purifying phenol, since it has less activity than the one produced according to the proposed process. Specifically, it does not purify the finished product to the required extent in regard to its content of 2-methylbenzofuran.

The process for preparing the proposed composition of the catalyst for purifying phenol that is produced by decomposition of cumyl hydroperoxide comprises the stages of precipitating aluminum and zirconium hydroxide, sulfating the hydroxides, peptizing the electrolyte solution, screw extruding the catalyzed mass, and heat treatment. The starting aluminum compound that is used is aluminum hydroxide, consisting of boehmite and pseudoboehmite in a mass ratio of 1:3 to 3:1 (calculated on the basis of aluminum oxide). An aqueous sulfuric acid solution is used as the peptizing agent and is introduced into the catalysis mass at the sulfation and peptization stages.

The essential characterizing features of the proposed process are the use of a mixture of boehmite and pseudoboehmite in the indicated ratio for preparing the compound, and also introducing sulfuric acid in two steps: at the stage of sulfation and at the stage of peptization of the catalysis mass. The catalyst produced according to the proposed process makes it possible to convert practically all the impurities that are present in the phenol, which serves as the starting material, into easily separable high-boiling compounds.

The industrial applicability of the proposed catalyst for the purification of phenol and the process of preparing it are confirmed by the following examples.

EXAMPLES

Example 1 a) Preparation of Catalyst 431 g of the salt $ZrOCl_2.8H_2O$ are dissolved in 5.2 L of distilled water. 332 mL of a $NH_4OH$ solution having a concentration of about 25% is dripped into the resulting solution over 20 minutes. The resulting precipitate is filtered off and washed with water on a Büchner funnel to remove ammonium chloride. The resulting washed precipitate is dried in a drying cabinet at 110° C. for 24 hours. The dried precipitate is ground in a mill, and the resulting fine powder is sifted through a 180 µm sieve. The mass of the powder is 190 g or 147 g, calculated on the basis of $ZrO_2$.

To sulfate the powder, it is treated with 1.14 L of 1 N sulfuric acid solution for 1 hour. Then, the resulting mixture is filtered to remove excess solution, and the product is dried at 110° C. (10 h) and is further used for molding.

To produce pseudoboehmite, 3 L of a 100 g/L sodium aluminate solution is used. The precipitation is performed by simultaneously pouring together the indicated aluminate solution and a 60% solution of nitric acid (yield: 1.8 L) at a temperature of 20–25° C. and at a pH in the range 9.1 to 9.5 over the course of 2 hours. After the solutions have been completely poured together, the suspensions are stabilized by boiling (102–105° C.) at a pH that is kept constant in the range 9.1–9.3 by adding sodium aluminate solution. The product is a suspension of glassy precipitate of pseudoboehmite containing 300 g of $Al_2O_3$.

To produce boehmite, 1 L of a 100 g/L sodium aluminate solution is used. The precipitation is performed by simultaneously pouring together the indicated aluminate solution and a 60% nitric acid solution (yield: 0.7 L) at a temperature of 102–105° C. (when boiling) and at a pH in the range 8.5 to 8.9 over the course of 2 hours. The product is a suspension of honey-like precipitate of boehmite containing 100 g of $Al_2O_3$.

The resulting suspensions of pseudoboehmite and boehmite are combined and washed on a Büchner funnel to remove the contaminating sodium nitrate salt. The washed precipitate is dried at 110° C. for 10 hours and ground into a fine powder all of which passes through a sieve having 0.25 mm openings. The calcining loss when the resulting dried mixed aluminum hydroxide powder is roasted at 850° C. is 24.6% by mass. The ratio of boehmite to pseudoboehmite in the aluminum hydroxide powder is 1:3, calculated on the basis of $Al_2O_3$.

After that, the powdered sulfated zirconium hydroxide is mixed with 83.6 g of powdered aluminum hydroxide in a Werner & Pfleiderer Z blade mixer, the solution is peptized with sulfuric acid solution (3.8 mL of 60% solution), and small portions of around 250 mL of water are added, bringing the moisture content (calcining loss) of the mass to 55% by mass. The resulting mass is molded in a screw extruder through a die having a hole diameter of 2 mm. The extrudates are dried for 8 hours at 110° C. and then roasted in a stream of dried air for 4 hours at 630° C.

Gross composition of the finished catalyst: 66.2% by mass of $ZrO_2$; 30% by mass of $\gamma$-$Al_2O_3$; 5.0% by mass of S. The total content of aluminum and zirconium sulfate in the catalyst was 15.0% (calculated on the basis of $SO_4$), and the total content of aluminum oxide and sulfate was 30% by mass (calculated on the basis of $Al_2O_3$).

b) Purification of Phenol

The test of the resulting aluminum zirconium catalyst for the process of purifying phenol was conducted at a temperature of 100° C. and a raw material volume feed rate of 1.5 $h^{-1}$ in a flow-through laboratory apparatus. The table below gives the composition of the phenol serving as the starting material, which was produced by decomposition of cumyl hydroperoxide and which was supposed to be purified, and the composition of the product of its catalytic purification on the prepared catalyst.

TABLE

Composition of starting phenol and catalytically purified phenol.

| | | Content (ppm) | |
|---|---|---|---|
| No. | Impurity | In starting phenol | In purified phenol |
| 1 | Hydroxyacetone (HA) | 200 | <1 |
| 2 | Mesityl oxide (MO) | 50 | <5 |
| 3 | α-Methylstyrene (AMS) | 5 | <1 |
| 4 | 2-Methylbenzofuran | 30 | 52 |
| 5 | Acetophenone (AP) | 5 | <1 |
| 6 | Dimethylphenylcarbinol (DMPC) | 10 | <1 |
| 7 | Total impurities | 300 | <61 |

The content of impurities in the phenol was determined by the method of gas chromatography on a "Kristall 2000M" chromatograph with a capillary column 25 m long using OV-1 as the stationary phase.

Example 2

The catalyst is prepared as in Example 1, but the ratio of boehmite to pseudoboehmite (calculated on the basis of $Al_2O_3$) in the mixed powdered aluminum hydroxide is 3:1. The zirconium hydroxide precipitate is sulfated with 380 ml of sulfuric acid solution. The quantity of mixed powdered aluminum hydroxide used for mixing with the powdered sulfated zirconium hydroxide is 13.9 g. The remaining parameters are the same as in Example 1.

The total content of aluminum and zirconium sulfates in the resulting sample of roasted (finished) catalyst, calculated on the basis of $SO_4$, was 5.0% by mass, and the total content of aluminum oxide and sulfate was 5% by mass, calculated on the basis of $Al_2O_3$.

The test of the resulting aluminum zirconium catalyst for the process of purifying phenol was conducted at a temperature of 110° C. and a raw material volume feed rate of $V=6\ h^{-1}$. The resulting phenol has the following composition (in ppm): HA<1; α-methylstyrene<1; 2-methylbenzofuran–50; OM<5; AP<1; and DMPC<1.

Example 3

A sample is taken of the aluminum zirconium catalyst whose preparation and composition are described in Example 1. The test is conducted according to the methods described above at a temperature of 90° C. and a raw material volume feed rate of $V=1\ h^{-1}$. The resulting phenol has the following composition (in ppm): HA<1; α-methylstyrene<1; 2-methylbenzofuran–58; OM<5; AP<1; and DMPC<1.

Example 4

A sample is taken of the aluminum zirconium catalyst, whose preparation and composition are described in Example 2. The test is conducted according to the methods described above at a temperature of 200° C. and a raw material volume feed rate of $V=1.5\ h^{-1}$. The resulting phenol has the following composition (in ppm): HA <1; α-methylstyrene<1; 2-methylbenzofuran-31; OM<5; AP<1; and DMPC<1.

What is claimed is:

1. A process for purifying raw phenol produced by the cumyl hydroperoxide cleavage method, which process comprises (i) contacting the raw phenol with an acidic aluminum oxide catalyst at a temperature of 90–200° C. and a raw material volumetric feed rate of $1\text{–}6\ h^{-1}$, and (ii) subsequently isolating purified phenol by distillation, wherein the aluminum oxide catalyst comprises a mixture of aluminum and zirconium oxides and sulfates and has a total content of aluminum and zirconium sulfate of from 5 to 15% by mass (calculated on the basis of $SO_4$ ions) and the catalyst has a total content of aluminum and oxide and sulfate of 5–30% mass (calculated on the basis of aluminum oxide).

2. The process according to claim 1, wherein the catalyst consists essentially of a mixture of aluminum and zirconium oxides and sulfates.

3. The process according to claim 2, wherein the catalyst is prepared by a process which comprises the steps of treating zirconium hydroxide twice using sulfuric acid in a first sulfation step and a second peptization step, and adding aluminum oxide in the peptizion step wherein aluminum oxide consists of a mixture of boehmite and pseudoboehmite in a mass ration of from 1:3 to 3:1.

* * * * *